(12) United States Patent
Cornish et al.

(10) Patent No.: US 8,100,837 B1
(45) Date of Patent: Jan. 24, 2012

(54) SUPERELASTIC GUIDEWIRE WITH LOCALLY ALTERED PROPERTIES

(75) Inventors: Wayne E. Cornish, Fallbrook, CA (US);
Sharon Wong, San Francisco, CA (US)

(73) Assignee: Abbott Cardiovascular Systems, Inc., Santa Clara, CA (US)

( * ) Notice: Subject to any disclaimer, the term of this patent is extended or adjusted under 35 U.S.C. 154(b) by 1708 days.

(21) Appl. No.: 09/746,144

(22) Filed: Dec. 21, 2000

(51) Int. Cl.
*A61B 5/00* (2006.01)

(52) U.S. Cl. ........................................................ 600/585

(58) Field of Classification Search .......... 600/433–435, 600/585; 604/523–532
See application file for complete search history.

(56) References Cited

U.S. PATENT DOCUMENTS

| | | | |
|---|---|---|---|
| 4,665,405 A | 5/1987 | Drabowitch et al. | |
| 4,925,445 A | 5/1990 | Sakamoto et al. | |
| 4,984,581 A | 1/1991 | Stice | |
| 5,067,957 A | 11/1991 | Jervis | |
| 5,230,348 A | 7/1993 | Ishibe et al. | |
| 5,238,004 A | 8/1993 | Sahatjian et al. | |
| 5,243,996 A | 9/1993 | Hall | |
| 5,341,810 A | 8/1994 | Dardel | |
| 5,341,818 A * | 8/1994 | Abrams et al. ................ | 600/585 |
| 5,411,476 A | 5/1995 | Abrams et al. | |
| 5,443,907 A * | 8/1995 | Slaikeu et al. ................ | 428/375 |
| 5,637,089 A | 6/1997 | Abrams et al. | |
| 5,722,981 A * | 3/1998 | Stevens ......................... | 606/148 |
| 5,749,837 A | 5/1998 | Palermo et al. | |
| 5,948,184 A | 9/1999 | Frantzen et al. | |
| 6,039,699 A | 3/2000 | Viera | |
| 6,106,488 A | 8/2000 | Fleming et al. | |
| 6,113,557 A | 9/2000 | Fagan et al. | |
| 6,325,766 B1 * | 12/2001 | Anderson et al. ............. | 600/585 |
| 6,375,629 B1 * | 4/2002 | Muni et al. .................... | 600/585 |
| 6,428,317 B1 * | 8/2002 | Abel ............................... | 433/102 |

FOREIGN PATENT DOCUMENTS

JP             04187159 A  *  7/1992

* cited by examiner

*Primary Examiner* — Max HIndenburg
*Assistant Examiner* — Jonathan M Foreman
(74) *Attorney, Agent, or Firm* — Finnegan, Henderson, Farabow, Garrett & Dunner LLP

(57) ABSTRACT

A guidewire formed at least in part of a superelastic member with a section having one or more altered properties including physical and mechanical properties. Preferably, the section of altered property has reduced superelasticity with respect to the remainder of the superelastic member. The invention also comprises method of manufacturing such guidewires wherein a section of the superelastic member is isolated and treated to change one or more of the properties. The treatment may be alloying with a diffusable element or isolating one or more sections to work and heat treat to decrease superelasticity relative to the rest of the member. The section having one or more altered properties is preferably a distal portion of the member, for example about the most distal 3 cm.

8 Claims, 1 Drawing Sheet

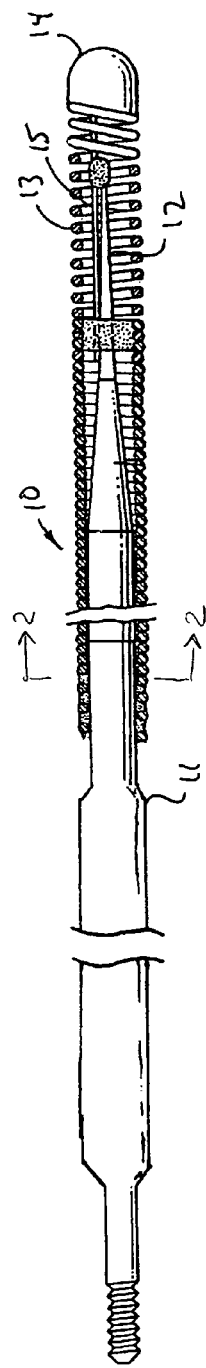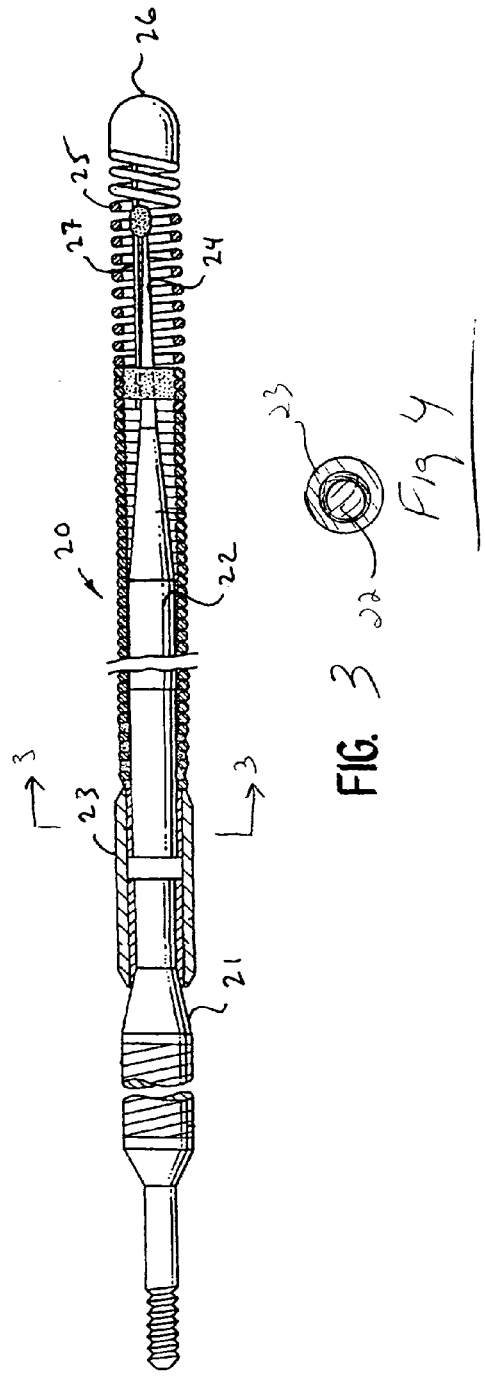

SUPERELASTIC GUIDEWIRE WITH LOCALLY ALTERED PROPERTIES

BACKGROUND OF THE INVENTION

Elongated guiding members are widely used in medical procedures. A common example are the guidewires used to deliver intravascular devices such as angioplasty catheters. Since guidewires must traverse the peripheral and tortuous coronary vasculature in order to reach the desired treatment location, they must exhibit a number of important characteristics. Specifically, a guidewire should have sufficient strength and elasticity to impart suitable pushability, trackability, torqueability, flexibility and handleability. A major requirement for guidewires and other guiding members, whether they be solid wire or tubular members, is that they have sufficient column strength to be pushed through a patient's tortuous vascular system or other body lumen without kinking. However, they must also be flexible enough to avoid damaging the blood vessel or other body lumen through which they are advanced. Efforts have been made to improve both the strength and flexibility of guidewires to make them more suitable for their intended uses, but these two properties are for the most part diametrically opposed to one another in that an increase in one usually involves a decrease in the other.

Prior art guidewire designs have made use of shape memory and/or superelastic alloys such as nickel-titanium ("Nitinol"). The shape memory characteristics allow the devices to be deformed to facilitate their insertion into a body lumen or cavity and then be heated within the body so that the device returns to its original shape. Superelastic characteristics on the other hand generally allow the metal to be deformed and restrained in the deformed condition to facilitate the insertion of the medical device containing the metal into a patient's body, with such deformation causing the phase transformation from austenite to martensite. Once within the body lumen the restraint on the superelastic member can be removed, thereby reducing the stress therein so that the superelastic member can return to its original undeformed shape by transformation back to the original austenite phase.

Despite the advantages offered by the use of superelastic and shape memory alloys, prior art designs have often suffered from insufficient performance characteristics. For example, U.S. Pat. No. 4,925,445 (Sakamoto et al.) discloses the use of a nickel-titanium superelastic alloy in an intravascular guidewire which could be processed to develop relatively high yield strength levels. However, at the relatively high stress levels which cause the austenite-to-martensite phase transformation characteristic of the material, the material of Sakamoto et al. did not have a very extensive stress-induced strain range in which the austenite transforms to martensite at relative constant stress. As a result, frequently as the guidewire was being advanced through a patient's tortuous vascular system, it could be inadvertently stressed beyond the superelastic region, i.e. develop a permanent set or even kink which can result in tissue damage. This permanent deformation would generally require the removal of the guidewire and the replacement thereof with another. Alternatively, U.S. Pat. No. 4,665,905 (Jervis) teaches alloys having extensive strain ranges, but the relatively constant stress level at which the austenite phase transformed to martensite was very low.

Accordingly, there remains a need for guidewires formed of superelastic alloy material having superior performance characteristics. Specifically, there is a need for such guidewires that have sufficient stiffness to exhibit good pushability coupled with superelastic properties that maximize flexibility and minimize kinking. This invention satisfies these and other needs.

SUMMARY OF THE INVENTION

The invention is directed to an elongated guiding member for medical devices, such as a guidewire, comprising a superelastic member having at least one section with one or more altered properties, which may be mechanical or physical properties. Preferably, the altered property comprises a section of the superelastic member that exhibits reduced superelasticity with respect to the rest of the superelastic member. The reduction in superelasticity can be quantified by the permanent set, in units of strain, that is measured after tensile loading to high levels of strain, approximately but not limited to 8%. Preferably, the permanent set is less than 0.5%. For example, the section of the guidewire having altered properties can comprise the distal tip of the superelastic member, preferably at least about 3 cm of the distal end. In some embodiments, the superelastic member may include substantially the entire length of the guidewire. In other embodiments, the guidewire comprises a distal superelastic member secured to a relatively stiff elongated proximal member. The distal and proximal members may be secured by a tubular connecting element or the respective ends of the distal and proximal members may be configured to mate with each other. Preferably, the superelastic member of the guidewire comprises a nickel-titanium alloy.

The invention is also directed to methods of manufacturing an elongated medical device, such as a guidewire, having a superelastic member with a section having one or more altered properties. In one embodiment, the method includes providing an elongated superelastic member, such as for a guidewire, atmospherically isolating a section of the superelastic member and alloying the isolated section by exposing the section to a diffusable element. The superelastic member may be formed into the elongated medical device or a part of the device either before or after treatment to alter the physical or the mechanical properties of the superelastic member. Preferably, the diffusable element comprises an easily diffusable element such as oxygen, hydrogen, carbon or nitrogen or mixtures thereof. Alloying the section reduces the superelasticity of the section as compared with the rest of the superelastic member.

In a second embodiment, the method includes providing a NiTi member of a guidewire, cold-working an isolated section of the superelastic NiTi member, and then heat treating the cold worked section of the NiTi member. Preferably, this decreases the superelasticity of the treated section of the NiTi member relative to the rest of the NiTi member. Heat treating the isolated section of the superelastic member comprises exposing the section to a temperature ranging from about 250° C. to about 800° C. for a period of time ranging from about 5 minutes to about 40 minutes.

BRIEF DESCRIPTION OF THE DRAWINGS

FIG. 1 is schematic view, partially in section, of a guidewire embodying features of the invention.

FIG. 2 is a transverse cross-sectional view of the guidewire shown in FIG. 1 taken along the lines 2-2.

FIG. 3 is a schematic view, partially in section, of another embodiment of a guidewire having features of the invention.

FIG. 4 is a transverse cross-sectional view of the guidewire shown in FIG. 3 taken along the lines 4-4.

DETAILED DESCRIPTION OF THE INVENTION

FIGS. 1 and 2 illustrate a guidewire 10 embodying features of the invention that is adapted to be inserted into a patient's body lumen, such as an artery. The guidewire 10 comprises an elongated core member 11 formed from a superelastic material. A distal section 12 of elongated core member 11 has been processed so that it exhibits performance characteristics different from the rest of core member 11. Here, about the distal 3 cm has reduced superelasticity as compared with the remainder of core member 11. Guidewires configured for other applications can have different sections and different lengths that exhibit the altered properties. Depending upon the desired application, core member 11 may be either solid or tubular. A helical coil 13 is disposed about the distal portion of core 11 and has a rounded plug 14 on the distal end thereof. The coil 13 is secured to the distal member at a proximal location and at intermediate location by a suitable solder. A shaping ribbon 15 is secured by its proximal end to the distal member and by the distal end thereof to the rounded plug 14 which is usually formed by soldering or welding the distal end of the coil 13 to the distal tip of the shaping ribbon 15.

Preferably, the most distal section of the helical coil 13 is made of radiopaque metal such as platinum, platinum-nickel alloys or palladium to facilitate the fluoroscopic observation while it is disposed within a patient's body. Also preferably, a portion of elongated core member 11 proximal of the helical coil 13 is coated with a lubricous coating to facilitate travel within a guiding catheter or a bodily lumen. Suitable coatings include polytetrafluoroethylene (sold under the trademark Teflon by du Pont, de Nemours & Co.), polysiloxane and the like.

FIGS. 3 and 4 illustrate an alternate embodiment of the invention, showing guidewire 20 that has an elongated, relatively high strength proximal member 21, a relatively short distal member 22 which is formed substantially of superelastic alloy material and a connector element 23. A section 24 of distal member 22 has been processed so that it has altered properties affecting performance characteristics different from the rest of distal member 22. Depending on the application, proximal member and connector element may be formed from superelastic materials, metal such as stainless steel, composite materials and the like.

Preferably, proximal member 21 is coated with a lubricous coating to facilitate travel within a catheter or a bodily lumen. Suitable coatings include polytetrafluoroethylene (sold under the trademark Teflon by du Pont, de Nemours & Co.), polysiloxane and the like.

Connector element 23 connects the proximal end of the distal member 22 to the distal end of the proximal member 21 into a torque transmitting relationship. The connector element 23 is a hollow tubular shaped element having an inner lumen extending therein which is configured to receive the respective ends of the proximal and distal members. The ends may be press fit into the connector element or they may be secured therein by crimping or swaging the connector or by means such as a suitable adhesive or by welding, brazing or soldering. In other embodiments, one of skill in the art can configure the respective ends of the proximal and distal members to mate with each other without a connector element.

The distal member 22 has at least one tapered section that becomes smaller in the distal direction. A helical coil 25 is disposed about the distal member 22 and has a rounded plug 26 on the distal end thereof. The coil 25 is secured to the distal member 22 at proximal location and at intermediate location by a suitable solder. A shaping ribbon 27 is secured by its proximal end to the distal member 22 by the solder and by the distal end thereof to the rounded plug 26 which is usually formed by soldering or, welding the distal end of the coil 25 to the distal tip of the shaping ribbon 26. Preferably, the most distal section of the helical coil 25 is made of radiopaque metal such as platinum, platinum-nickel alloys or palladium to facilitate the observation thereof while it is disposed within a patient's body.

The present invention provides guidewires that have superelastic characteristics to facilitate the advancing thereof in a body lumen. The guiding members exhibit extensive, recoverable strain resulting from stress induced phase transformation of austenite to martensite at exceptionally high stress levels which greatly minimizes the risk of damage to arteries during the advancement therein.

Alloys having shape memory/superelastic characteristics generally have at least two phases, a martensite phase, which has a relatively low tensile strength and which is stable at relatively low temperatures, and an austenite phase, which has a relatively high tensile strength and which is stable at temperatures higher than the martensite phase. Shape memory characteristics are imparted to the alloy by heating the metal at a temperature above which the transformation from the martensite phase to the austenite phase is complete, i.e. a temperature above which the austenite phase is stable. The shape of the metal during this heat treatment is the shape "remembered". The heat treated metal is cooled to a temperature at which the martensite phase is stable, causing the austenite phase to transform to the martensite phase. The metal in the martensite phase is then plastically deformed, e.g. to facilitate the entry thereof into a patient's body. Subsequent heating of the deformed martensite phase to a temperature above the martensite to austenite transformation temperature causes the deformed martensite phase transform to the austenite phase and during this phase transformation the metal reverts back to its original shape.

The superelastic members of the invention are preferably made of an alloy material consisting essentially of about 30 to about 52% titanium and the balance nickel and up to 10% of one or more other alloying elements. The other alloying elements may be selected from the group consisting of iron, cobalt, vanadium, platinum, palladium and copper. The alloy can contain up to about 10% copper and vanadium and up to 3% of the other alloying elements. The addition of nickel above the equiatomic amounts with titanium and the other identified alloying elements increase the stress levels at which the stress-induced austenite-to-martensite transformation occurs and ensure that the temperature at which the martensite phase transforms to the austenite phase is well below human body temperature so that austenite is the only stable phase at body temperature. The excess nickel and additional alloying elements also help to provide an expanded strain range at very high stresses when the stress induced transformation of the austenite phase to the martensite phase occurs. The addition of small amounts of up to about 3% platinum and/or palladium provides increased radiopacity.

Preferably the composition and thermomechanical processing are controlled to provide a thermally stable austenite phase at body temperature (i.e. 37° C.) which converts to the martensite phase when placed under sufficient stress. See for example the compositions and processing described in U.S. Pat. Nos. 5,341,810 (Abrams et al.) and 5,637,089 (Abrams et al.) where are incorporated herein in their entireties.

The guidewires of the invention are generally about 130 cm to about 300 cm in length with an outer diameter of about 0.006 to 0.018 inch, including the lubricous coating, for guidewires adapted for coronary artery use. Larger diameter guidewires may be employed in peripheral arteries and other body lumens. The helical coil may be about 10 to about 45 cm in length, has an outer diameter about the same size as the diameter of the elongated core member, and is made from wire about 0.002 to 0.003 inch in diameter.

A first method for manufacturing guidewires having characteristics of the invention comprises alloying a section of the superelastic member so that it has altered properties. Preferably, the section of the superelastic member in which the altered properties are desired is atmospherically isolated from the remainder of the superelastic member. For example, that section of the wire can be placed in a pressure chamber. Next, the section can be exposed in the chamber to an atmosphere enriched with one or more of the desired alloying element preferably at elevated temperatures and pressures. Easily diffusable elements such as hydrogen or oxygen are preferable, but other alloying elements such as carbon or nitrogen may be used. Alloying the isolated section of the superelastic member varies one or more of the properties of the superelastic material. It is currently desired to selectively reduce the superelasticity of the material at the distal tip of the guidewire. For example, a guidewire having reduced superelasticity in about the distal 3 cm provides desirable performance characteristics.

Alternatively, a section having one or more altered properties in a superelastic guidewire can be created by thermal treatment. In general, the superelastic member of the guidewire is cold-worked to reduce the superelasticity of a section of the member. Then, this cold worked section heat treated to recover some ductility lost during cold working and thereby reducing the superelasticity of the section. The cold work can be performed by drawing, rolling and other conventional working methods The ability to tailor the superelastic and shape memory characteristics in varying sections of the guidewire permits the design of guidewires having superior performance characteristics. For example, a currently preferred guidewire has reduced superelasticity in about the distal 3 cm. Preferably, the step of heat treating the superelastic member comprises exposing the superelastic member to a temperature between about 250° C. and about 800° C. for a period of about 5 to about 40 minutes.

A presently preferred method for forming the superelastic member of the guide wire prior to isolation and treatment of one or more sections thereof is to cold work, preferably by drawing, a rod or tubular member having a composition according to the relative proportions described above and then heat treating the cold worked product while it is under stress to impart a shape memory thereto. If the final product is to be tubular, a small diameter ingot may be formed into a hollow tube by extruding or by machining a longitudinal center hole therethrough and grinding the outer surface thereof smooth. Before drawing the solid rod or tubular member, it is preferably annealed at a temperature of about 500° to about 750° C., typically about 650° C., for about 30 minutes in a protective atmosphere such as argon to relieve essentially all internal stresses. In this manner all of the specimens start the subsequent thermomechanical processing in essentially the same metallurgical condition so that products with consistent final properties are obtained. Such treatment also provides the requisite ductility for effective cold working.

The stressed relieved stock is cold worked by drawing to effect a reduction in the cross sectional area thereof of about 30 to about 70%. As used herein percent cold work refers to the percent reduction of the transverse cross-sectional area. The metal is drawn through one or more dies of appropriate inner diameter with a reduction per pass (i.e. cold work) of about 10 to 50%. Other forms of cold working can be employed such as rolling or swaging. Superelasticity may be imparted following cold work, with the drawn wire or hollow tubular product heat treated at a temperature between about 350° and about 600° C. for about 0.5 to about 60 minutes. Preferably, the drawn wire or hollow tubular product is simultaneously subjected to a longitudinal stress between about 5% and about 50%, preferably about 10% to about 30% of the tensile strength of the material (as measured at room temperature) in order to impart a straight "memory" to the metal and to ensure that any residual stresses therein are uniform. This memory imparting heat treatment also fixes the austenite-martensite transformation temperature for the cold worked metal. By developing a straight "memory" and maintaining uniform residual stresses in the superelastic material, there is little or no tendency for a guidewire made of this material to whip when it is torqued within a patient's blood vessel.

An alternate method for imparting a straight memory to the cold worked material includes mechanically straightening the wire or tube and then subjecting the straightened wire to a memory imparting heat treatment at a temperature of about 300° to about 450° C., preferably about 330° to about 400° C. The latter treatment provides substantially improved tensile properties, but it is not very effective on materials which have been cold worked above 55%, particularly above 60%. Materials produced in this manner exhibit stress-induced austenite to martensite phase transformation at very high levels of stress but the stress during the phase transformation is not nearly as constant as the previously discussed method. Conventional mechanical straightening means can be used such as subjecting the material to sufficient longitudinal stress to straighten it.

It will be apparent from the foregoing that, while particular embodiments of the invention have been illustrated and described herein, various modifications can be made without departing from the spirit and scope of the invention. Moreover, those skilled in the art will recognize that features shown in one embodiment may be utilized in other embodiments.

What is claimed is:

1. An elongated device for medical procedures comprising a superelastic member having a first section with a first set of properties and an adjacent second section having a second set of properties which have been altered from the first set of properties by treating the second section with an easily diffusable element, wherein said easily diffusable element is selected from the group consisting of oxygen, hydrogen, and nitrogen, and the superelastic member comprises a nickel-titanium alloy.

2. The elongated device of claim 1, wherein the easily diffusable element is hydrogen.

3. The elongated device of claim 1, wherein the easily diffusable element is oxygen.

4. The elongated device of claim 1, wherein the altered properties comprise reduced superelasticity.

5. The elongated device of claim 1, wherein the second section of the superelastic member having the altered properties comprises a distal end of the superelastic member.

6. The elongated device of claim 5, wherein the distal end is at least about 3 cm in length.

7. The elongated device of claim 5, wherein the altered properties comprise reduced superelasticity.

8. The elongated device of claim 7, wherein the distal end is at least about 3 cm in length.

\* \* \* \* \*